United States Patent [19]

Herschler

[11] Patent Number: 4,973,605

[45] Date of Patent: Nov. 27, 1990

[54] USE OF METHYLSULFONYLMETHANE TO RELIEVE PAIN AND RELIEVE PAIN AND NOCTURNAL CRAMPS AND TO REDUCE STRESS-INDUCED DEATHS IN ANIMALS

[76] Inventor: Robert J. Herschler, 3080 NW. 8th Ave., Camas, Wash. 98607

[21] Appl. No.: 385,117

[22] Filed: Jul. 26, 1989

Related U.S. Application Data

[60] Division of Ser. No. 878,949, Jun. 26, 1986, Pat. No. 4,863,748, Continuation of Ser. No. 727,989, Apr. 29, 1985, Pat. No. 4,616,039, and a continuation-in-part of Ser. No. 601,771, Apr. 17, 1984, Pat. No. 4,559,329, and a continuation-in-part of Ser. No. 584,354, Feb. 28, 1984, Pat. No. 4,568,547, and a continuation-in-part of Ser. No. 418,110, Sep. 14, 1982, Pat. No. 4,514,421, which is a continuation-in-part of Ser. No. 277,592, Jun. 26, 1981, Pat. No. 4,477,469, Division of Ser. No. 71,068, Aug. 6, 1979, Pat. No. 4,296,130.

[51] Int. Cl.$^5$ .............................................. A61K 31/10
[52] U.S. Cl. .................................................... 514/708
[58] Field of Search ......................................... 514/708

Primary Examiner—Stanley J. Friedman
Attorney, Agent, or Firm—Millen, White & Zelano

[57] ABSTRACT

Methylsulfonylmethane is effective to relieve pain and nocturnal cramps and to reduce stress-induced deaths in ainmals.

14 Claims, No Drawings

USE OF METHYLSULFONYLMETHANE TO RELIEVE PAIN AND RELIEVE PAIN AND NOCTURNAL CRAMPS AND TO REDUCE STRESS-INDUCED DEATHS IN ANIMALS

This application is a division of application Ser. No. 878,948, now U.S. Pat. No. 4,863,748, filed June 26, 1986, as a continuation-in-part of applications Ser. No. 727,989, now U.S. Pat. No. 4,616,039, filed Apr. 29, 1985; Ser. No. 601,771, now U.S. Pat. No. 4,559,329, filed Apr. 17, 1984, Ser. No. 584,354, now U.S. Pat. No. 4,568,547, filed Feb. 28, 1984 and Ser. No. 418,110, now U.S. Pat. No. 4,514,421, filed Sept. 14, 1982, as continuations-in-part of application Ser. No. 277,592, now U.S. Pat. No. 4,477,469, filed June 26, 1981, as a division of Ser. No. 071,068, now U.S. Pat. No. 4,296,130, filed Aug. 6,1979, all of whose disclosures are incorporated herein by reference.

BACKGROUND OF THE INVENTION

This invention relates to uses of methylsulfonylmethane (MSM ®).

In my prior U.S. Pat. No. 4,296,130, I disclose compositions containing methylsulfonylmethane to soften, smooth, lubricate and preserve the pliancy of human tissues and for reducing the brittleness of finger and toe nails. I disclose therein that methylsulfonylmethane is substantially inert to the chemistry of the body and, because of its extremely low toxicity and inertness to the diverse chemical reactions involved in the life processes, it can be used as a diluent for blood. The ingestion of oral compositions is disclosed therein to preserve the pliancy of intestinal and other tissue U.S. 4,477,469 relates to methylsulfonylmethane and carbamide compositions. U.S. Pat. No. 4,514,421 relates to methods of ameliorating symptoms of stress of allergy with methylsulfonylmethane.

U.S. Pat. No. 4,296,104 discloses DMSO compositions which optionally can contain a protein modifying agent, such as methylsulfonylmethane. U.S. Pat. No. 4,112,946 discloses the use of an aqueous solvent system comprising methylsulfonylmethane in a process for the introduction of a health modifying agent into water-living animals as an osmotic factor. S.N. 584,354 relates to the use of methylsulfonylmethane as the diluent or carrier for storage unstable pharmaceutically active agents. S.N. 601,771 relates to oral pharmaceutical compositions comprising a gastointestinal upset-promoting pharmaceutical and ameliorating amount of methylsulfonylmethane.

J.J. Kocsis et al, Annals N.Y. Acad. Sci. 243, 104–109 (1975), cite literature which report that methylsulfonylmethane, a known metabolite of dimethylsulfoxide, persists for as long as three weeks after percutaneous application in man and one week after i.v. administration. The authors report that methylsulfonylmethane, like DMSO, enhances urinary taurine secretion produced by aromatic hydrocarbons in man, antagonizes the lethal effects of anticholinesterases such as paraoxon, tetraethyl pyrophosphate and octamethyl pyrophosphoramide; lowers the body temperature of rats exposed to 5° C. temperature; and reduces motor activity (when administered i.p.). Kulshestha et al, C.A. 83; 22910n (1975), report that methylsulfonylmethane occurs naturally in a variety of fruits, vegetables and vegetable products, grains in at least trace amounts ( 3.3 ppm). T.W. Pearson et al, C.A. 95:113654w (1981). It is present in small amounts in normal urine. Williams et al, Archs. Biochem. Biophys. 1966, 113, 251-2. The following Chemical Abstracts refer to the biological aspects of methylsulfonylmethane as a DMSO metabolite, in cattle, 83:183a; Escherichia coli inhibition by, 83:72577e; nervous system depression by, 84:173608a; Salmonella typhimurium inhibition by, 82:71; of urine, 75:86025v; heart response to, 74:2429y; lung constrictivity activity of, 62:9634f; in tissue culture protection against X-rays, 58:9391e; toxicity of, ETOH and, 64:7229h; in urine after administration of, 65:17537g; in urine of humans, 64:10170g; and in urine as methylsulfonylmethane metabolite, 64:7213a; 65:17535b.

Siegel, (1985, Private Communication) has evaluated methylsulfonylmethane in mice with a genetic predisposition to a form of cancer and rheumatoid arthritis. The sulfone was administered orally. There was a significant delay in the development of lymphomas as well as decreased tumor incidence, compared with control. In addition and only grossly examined, treated animals demonstrated a marked reduction in joint involvement. An increased titer of primary IgM and secondary IgG was measured.

In a separate pilot study, female rats given an abdominal application of DMBA while receiving methylsulfonylmethane in their drinking water did not develop tumors, while mammary tumors were seen in control animals. Waltering, G. and James, A. (1985, Private Communication).

Metcalf, L., L. Equine Vet. Sci. 3(5):148–174 (1983) describes the benefits observed when methylsulfonylmethane was added to the diet of animals. One disorder, epiphysitis, involving calcium/phosphorous imbalance in the horse was rapidly corrected with oral methylsulfonylmethane.

I have found that notwithstanding its extreme lack of toxicity and inertness of the diverse chemical reactions involved in the life processes, surprisingly methylsulfonylmethane nevertheless is metabolized sufficiently to supply the nutritional sulfur requirements of animals, including humans and other vertebrates, whose diet is deficient in assimilable sulfur. The incidence of such assimilable sulfur-deficient diets is very high because of the high percentage of processed foodstuffs therein in advanced cultures.

I have also found that in addition to the pharmacologically beneficial effects methylsulfonylmethane has in humans and other animals which are specifically disclosed in my parent applications, it is useful in the treatment of a surprising variety of other diseases and adverse physiological conditions, as disclosed in detail hereinafter.

Since the early part of 1983, methylsulfonylmethane has been sold in tablet form (250 mg) as a dietary supplement.

OBJECTS OF THE INVENTION

It is an object of this invention to provide a method for treating diverse and adverse physiological conditions in humans and other animals with methylsulfonylmethane.

Upon further study of the specification and appended claims, further objects and advantages of this invention will become apparent to those skilled in the art.

SUMMARY OF THE INVENTION

In a method-of-use aspect, this invention relates to a method of ameliorating the pain and discomfort associated with arthritis in an animal which comprises administering to an animal manifesting overt symptoms of the disease an amount of methylsulfonylmethane effective to ameliorate the pain.

In another method-of-use aspect, this invention relates to a method of alleviating intractible pain, which comprises administering intravenously to a patient suffering from a disease producing such pain an amount of methylsulfonylmethane effective to alleviate the pain.

In another method-of-use aspect, this invention relates to a method of inhibiting nocturnal and arthritic and activity-induced muscle cramps in a person having a propensity for such muscle cramps, which comprises orally administering thereto an amount of methylsulfonylmethane effective to inhibit the muscle cramps.

In other method-of-use aspects this invention relates to the treatment of other adverse physiological conditions with methylsulfonylmethane including the pharmacological uses described hereinafter.

Other aspects of this invention will be apparent to those skilled in the art to which this invention pertains.

DETAILED DISCUSSION

Notwithstanding the fact that methylsulfonylmethane is omnipotent in body fluids and is so non-toxic that it can be used as a diluent for blood without upsetting the blood chemistry, as disclosed and claimed in U.S. Pat. No. 4,514,421 and S.N. 601,777, at daily dosages of at least about 100 mg, methylsulfonylmethane is an ameliorating agent for a variety of pathological conditions when administered systemically and preferably orally to persons displaying symptoms of physiological response to stress, e.g., gastrointestinal distress, inflammation of the mucous membranes and allergic reactions.

Methylsulfonylmethane and many precursor compounds which are readily converted to methylsulfonylmethane in the body, are normal ingredients found in most natural, i.e., unprocessed foods consumed by man and other animals. Methylsulfonylmethane and its precursors have been available as nutritional and possibly essential factors in the vertebrate diet long before terrestrial life occurred. Methylsulfonylmethane has multiple functions in the body. At low levels of ingestion, it functions as a normal dietary ingredient, viz., as a food or food ingredient; at higher levels it functions as a pharmaceutically active agent.

Sulfur also plays important roles in the body, including the forming of "tie-bars" or disulfide bonds holding molecular strands of connective tissue together. It plays many other essential roles, such as determining the contour of diverse biomolecules, and is essential to the activity of many enzymes that protect and sustain life processes. To perform these roles, constant intake of assimilable sulfur is needed by the body. Heretofore, it was believed that ingested protein supplied sufficient metabolic sulfur for balanced nutritional needs. However, it now appears that this is not the case and that methylsulfonylmethane ingestion is required in order to maintain nutritionally adequate levels of assimilable sulfur in the body. While it was known for several decades that methylsulfonylmethane was a normal constituent of the body, there was no recognition of the importance of its role in animal nutrition and good health. With today's modern diet of cooked and otherwise processed and diluted foods, most if not all diets of civilized man and domesticated lower animals are deficient in this critically important ingredient.

Methylsulfonylmethane is a key nutritional ingredient, available and assimilated by all plant and animal life from their beginnings on earth. It is essential to a healthful diet and is a nutritional essence found in almost every fresh food of any origin now consumed by animal life. However, it is volatile and therefore readily becomes lost when fresh food is processed and/or stored.

It is known that many foodstuffs are altered by conventional processing. For example, proteins are denatured or altered so that water soluble proteins become insoluble and insoluble protein becomes soluble, for example, the insolubilization of egg white by cooking and the conversion of collagen to soluble gelatin. Fats are altered when processed or stored and starches can be rendered either more or less digestible. The average diet thus is deficient in methylsulfonylmethane because it is readily lost during conventional food processing, such as heating, drying or dehydrating, dilution with synthetic fillers and other poorly nutritional additives, cooking, radiation or pasteurizing, and long-term storage. Thus, methylsulfonylmethane is similar to vitamins and minerals which, as a general rule are also partially or totally lost during normal processing.

Generally speaking, processing any food, as by heating or drying, essentially eliminates the biologically important, sulfur-rich (about $\frac{1}{3}$ by wt. of sulfur) methylsulfonylmethane. Sulfur, a required macronutrient, must be constantly replaced in the mature animal and supplied for growth and good health in the young animal. An aspect of this invention is the discovery that methylsulfonylmethane is a preferred dietary source of sulfur. Although methionine, a sulfur-containing aminoacid, may serve as a partial back-up source during biometabolism where the diet is methylsulfonylmethane deficient, methionine demonstrates undesirable toxicity parameters.

Studies to date indicate that it is desirable that animals ingest about 0.5-1.0 milligram/kg body weight/day of methylsulfonylmethane to maintain optimum good health. However, any lower level will serve some benefit. Higher levels are either stored in the body as a sulfur reserve, provide a sufficient concentration to optimize synthesis of the multitude of required sulfur containing biomolecules, or simply are excreted as by the renal pathway or through the skin. The intact molecule has been shown to beneficially effect tissue, as for example improving the pliability and softness of the skin.

It is also important to recognize that alternate food sources of utilizable sulfur in the diet are most costly and the most difficult foods to generally obtain worldwide, for example fresh meat and fish. While fresh, unprocessed foods of plant and animal origin are the richest natural sources of methylsulfonylmethane, at best these are generally plentiful only seasonally. For geographic, political, religious, cultural and economic reasons, man and lower animals heretofore are believed to have suffered an unrecognized dietary deficiency preventing optimum health. This invention resolves this problem.

An individual consuming only unpasteurized milk, raw fish and meats, and uncooked, fresh vegetables and other plant-derived foods probably would derive sufficient naturally occurring methylsulfonylmethane and therefore not require sulfur supplements to the diet. Obviously this is impossible to achieve with customary meal preparation, food handling and storage. For example, milk, a food relatively rich in naturally occurring methylsulfonylmethane, loses a substantial portion of this compound as well as precursors, when subject to pasteurization to protect the product from microbial decomposition. Milk that has been spray dried, ordinarily is totally devoid of methylsulfonylmethane.

Domestic animals are dependent on man for their nutritional requirements. Because the majority of the food sources of domestic animals is now processed food, their diets are similarly subject to loss of valuable nutrients, including methylsulfonylmethane, during processing. Man cooks most foods and thus drives off most, if not all naturally occurring methylsulfonylmethane together with the precursors, and, accordingly, suffers a greater methylsulfonylmethane deficiency than any other animal.

As a basic supplier of metabolizable sulfur, methylsulfonylmethane is a foodstuff as well as being a natural ingredient of various foodstuffs. There are few, if any, natural and synthetic agents ingested by man and other animals as part of their diets that would not be improved nutritionally by methylsulfonylmethane being added thereto. Man and lower animals require about 1 mg/kg body weight of methylsulfonylmethane per day to replace the naturally occurring methylsulfonylmethane now lost in food processing.

Preferably, the methylsulfonylmethane is added to processed foods after processing has been completed and to heated foods immediately before serving. Although methylsulfonylmethane taken alone or as solid or liquid forms taken in the manner of minerals and vitamins would provide maximum benefits in maintaining good health, this procedure is not always possible. Therefore one must consider a wide variety of compositions which when ingested will supply the critical minimum of about 1 mg/kg body weight per day.

As well as processed foodstuffs, methylsulfonylmethane can be incorporated into salt, beverages, spices, conventional vitamin and mineral products and other orally ingested products, such as confectionary products and chewing gum.

In numerous testings, methylsulfonylmethane has been found to enhance the flavor and improves the taste of many ingested products including foods, beverages, condiments and pleasure items such as chewing gum, breath sweeteners, lozenges and similar compositions.

Methylsulfonylmethane may also be included in certain non-food products, as for example, tobacco products. This can be accomplished by adding methylsulfonylmethane dissolved in a tobacco humectant, such as a polyhydric alcohol. A burning cigarette would provide sublimed methylsulfonylmethane along with the smoke. Adding methylsulfonylmethane to the smoke enhances its flavor and taste.

This invention is based in part on the discovery that inorganic hydrogen sulfide and sulfate salts are not the primary sources of sulfur required to balance the natural sulfur cycle. It has been theorized that simple organic molecules such as the methyl-S-methane series (S=sulfenyl, sulfinyl or sulfonyl), available before or at the time the first simple life appeared on earth, are primary sources of the sulfur atom for sulfur containing biomolecules. Consistent with this proposal is the fact that methylsulfonylmethane is found naturally in most foods of plant and animal origin as well as all the water (as marine derived rain) falling on earth.

Sulfur is a required nutrient (food) for biological normalcy of plants as well as animals and methylsulfonylmethane plays a major role as the sulfur-rich food naturally available to man and lower vertebrates. The equation:

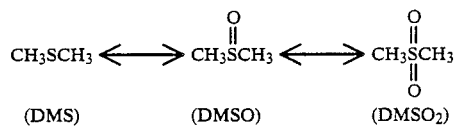

is essential to life forms and a minimum amount of methylsulfonylmethane in the daily diet is important, if not essential, for good to optimum health of man and lower vertebrates.

To understand the historic role of methylsulfonylmethane in life processes, one should begin at the beginning. From the primordial soup of life resident in the ancient seas, long before even the simplest terrestrial life forms appeared, algae and later phytoplankton produced organic molecules which released dimethyl sulfide to the atmosphere, an on-going process to this day. These simple forms of life, living in the upper or surface layer of the earth's oceans assimilated and converted inorganic sulfur into diverse organic molecules, mainly terniary dimethyl sulfonium salts. These terniary salts, by enzymatic and physical means, are broken down to methyl sulfide. Exemplary of these salts is dimethyl-beta-propiothetin, $(CH_3)_2S^+CH_2CH_2COOH$, which appears to be the most common organic sulfur containing molecule in marine plant life, (10% or more of the dry weight of some organisms). Dimethyl sulfide, a virtually water insoluble molecule which is even less soluble when "salted out" from marine waters, passes to the atmosphere in quantities sufficient to supply the sulfur needs for all terrestrial life forms. Volatile, nonpolar dimethyl sulfide moves to the upper atmosphere, sometimes called the ozone layer, where, catalyzed by sunlight, it is oxidized to the hygroscopic dimethyl sulfoxide (DMSO) and to methylsulfonylmethane. Both polar compounds dissolved in atmospheric moisture are delivered by rain to all land masses. Plant roots rapidly absorb and accumulate surprisingly high levels of these compounds, as determined by spectrophotometric and radiotracer techniques. The stable end products in plants, are methylsulfonylmethane and methionine, an essential amino acid, as well as other sulfur containing compounds naturally occurring in plants. A number of recent publications report that there is not enough hydrogen sulfide in the atmosphere to satisfy minimum cycle requirements and support this sulfur transport mechanism.

Challenger and Hayward reported in 1954 on the presence of dimethyl sulfonium salts, all precursors of methyl-S-methanes, in many marine and terrestrial plant forms serving as animal food. Since then, many scientific articles report on the natural occurrence of the methyl-S-methane series and the most stable member of the series (methylsulfonylmethane) in virtually every vegetable, nut, fruit, meat, fish and beverages as well as coffee, beer, tea and milk.

Metabolic sulfur was as important to life forms hundreds of millions of years ago as it is today. Before life "invented" the complex sulfur donor methionine (or cysteine), primitive life utilized the simpler methylsulfonylmethane and its precursors. Blue-green algae, which is found together with primitive bacteria in the earliest precambrian fossil remains, still grows widely today in the earth's surface waters and continues to produce DMS, helping to balance the sulfure equation of life. Considering that early life was programed to use methyl-S-methanes, one can understand why higher forms of life are genetically programmed to employ methylsulfonyl-methane as a sulfur donor. Therefore, methylsulfonylmethane is as acceptable and as assimilable to modern life forms as NaCl or water and thus presents an extremely low toxicity profile to at least the higher forms of life.

Methylsulfonylmethane and its precursors are as necessary for a good diet as is adequate potassium. The methyl-S-methane series, at food levels of up to about a hundred milligrams/day, supplies already normal, healthy tissue with maintenance levels of sulfur; with methionine and cystene degradation products also contributing though apparently not as directly nor as easily in. It is interesting that some forms of life can convert methionine to methylsulfonylmethane as well as the reverse synthesis sequence.

A number of biological effects of methylsulfonylmethane are described in my copending patent applications and issues patents cited above, as is the intentional ingestion of methylsulfonylmethane combinations as foods or flavorant ingredients thereof. The effect of high levels of methylsulfonylmethane ingestion in favorably altering the course of abnormal or disease states is believed to depend primarily on actions of the intact molecule. The major differences between the use of methylsulfonylmethane as a food and as a normalizer of biological function is the concentration and amount employed, dosage forms, and routes of systemic entry. As a food, methylsulfonylmethane plays an important role in the multitude of sulfhydryl (—SH) and disulfide (—S—S—) disruptions, destructions and repair associated with normal life processes. Systemic availability of methylsulfonylmethane for sulfur donation to repair and restore tissue damaged covalent disulfide bonds and synthesize having sulfhydryl groups critical to reactivity, is thus a basic nutritional requirement.

As with so many constituents of natural foods, excess amounts of methylsulfonylmethane are excreted unchanged from the body, the excretion routes being the feces, the renal pathway and through the skin. Orally ingested methylsulfonylmethane is stored to some degree in various organs, presumably banked for future sulfur needs of the body. The skin excretion route is unusual, particularly since about one-third of a given oral dose can be found in the perspiration. Like NaCl, excretion depends somewhat on perspiration rate. The accumulation in and excretion of methylsulfonylmethane from the skin is believed to account for its cosmetic effect, viz., more youthful appearing, pliable, blemish-reduced skin. Chemical and radiolabeled sulfur (35-S) assays can be used to determine the extent to which important biomolecules as heparin, insulin, co-enzyme A and other —SH bearing enzymes, biotin, methionine enkaphalin, human growth factor, hemoglobin, calcitonin, fibrinogen, muscle protein and other compounds derive their thiol (—S—) and disulfide (—S—S—) groups from methylsulfonylmethane and the possible preference of methylsulfonylmethane over S-content amino acids as the donor with such synthesis.

The word "food" broadly means a nutritive material taken into an organism for growth, work, protection, repair, restoration and maintenance of vital processes. Therefore, all animal life needs a continuing supply of food and cannot survive for long without it. However, food can also cause poor health and disease. Thus, balanced food intake or balanced nutrition are better definitions than "food" for the nutritional factor essential to good health. "Balanced food" implies that not only are all of the elements of good nutrition present, they are available in ample amounts for supplying the body's needs. Based on my findings with methylsulfonylmethane to date, a balanced food intake requires significant amounts of methylsulfonylmethane as a metabolic sulfur source, since all evidence suggests that no other ingredient or combination thereof, including methionine, cysteine, cystine and degradation products thereof, fulfills the role of methylsulfonylmethane.

The present invention relates to compositions and methods for replacing or supplementing methylsulfonylmethane, a natural but fugitive ingredient of food. Methylsulfonylmethane is lost from natural foods by virtually every known method of processing because although stable, it is quite volatile. It is, of course, absent in synthetic food additives, dietary mineral compositions, food substitutes and most fillers used to dilute or modify foods. It is also absent in "comfort" products, such as tobacco products, various alcoholic beverages, and cosmetic products such as toothpaste, mouth washes, breath sweeteners, and other similar agents that directly contact the mucous membranes of the buccal cavity and in some cases the entire respiratory tract, as in the case of cigarette smoke.

Using conventional analytical procedures, one can readily determine the naturally occurring methylsulfonylmethane (and/or its precursor) content of the cooked, processed and/or stored food and how it compares with the corresponding unaltered or natural food. For example, unprocessed milk from cows fed a nutritionally balanced feedstuff and permitted to field graze typically contains about 2-5 ppm of methylsulfonylmethane. In contradistinction, the methylsulfonylmethane content of unprocessed milk from cows fed dried animal feedstuffs and of milk and milk products which have been processed and pasteurized is negligible. One can readily calculate the amount of methylsulfonylmethane needed to restore milk, buttermilk, cream, yogurt, etc., to their "natural" levels. This is most conveniently accomplished at the bulk level, just before the milk or dairy product is to be bottled or packaged. Since other nutritional factors, such as Vitamin D, are customarily added to milk, the technology and equipment for such additions is conventional and readily available.

Many of the fruits and vegetables customarily consumed by humans contain approximately 1-4 ppm by weight of methylsulfonylmethane when freshly harvested. However, during processing, e.g., canning, most of the methylsulfonylmethane is lost. As in the case of dairy products, it is convenient to add the amount of methylsulfonylmethane required to restore it to its natural value to the processed product just prior to packaging or use.

It is apparent from the discussion above that superior nutritional benefits are obtained when methylsulfonylmethane is added to foodstuffs that do not require further processing, particularly processing requiring extended periods of heating or drying. Thus, it is preferable that methylsulfonylmethane be added to dairy products, canned fruits, desserts and other confections, vegetables, etc., which are not heated or which require only a minimum of warming prior to consumption.

Foodstuffs

Methylsulfonylmethane has, since 1983, been sold both as a food and food supplement for human consumption and its utility for such purposes has extensively been established. Its utility as a restorative additive in foodstuffs adapted for consumption by human beings or other animals has similarly been confirmed in a variety of species.

Examples of processed foodstuffs adapted for human consumption which typically have naturally occurring methylsulfonylmethane levels below about 0.25 ppm, are pasteurized milk and milk products, breakfast cereals, bread and other bakery products, canned fruits, vegetables, meats and fish and dried meats and fish.

Examples of processed foodstuffs adapted for domestic animal consumption which typically have naturally occurring methylsulfonylmethane levels below about 0.25ppm are dry, semi-dry and canned cat and dog foods; multi-ingredient feeds adapted for consumption by herbivores, poultry, swine, etc.

All of the foregoing products are processed in a manner which includes a heating and/or drying step which reduces their naturally occurring methylsulfonylmethane content to below about 0.25 pm. Methylsulfonylmethane can be admixed therewith after the aforesaid heating and/or drying step. e.g., after cooking in an open vessel at or above 100° C., to bring the methylsulfonylmethane content thereof to about 0.01 to 20 ppm, preferably about 1 to 15ppm, in the case of foodstuffs intended for human, dog or cat consumption, and about 0.01 to 20 ppm, preferably 1 to 10 ppm in the case of feed intended for consumption by a species of farm animal.

The methylsulfonylmethane can in some instances be admixed in crystalline form with one or more ingredients of the foodstuff as part of a final dry mixing step or as an aqueous, alcoholic or other ingestible solvent solution thereof, e.g., by spray mixing. Because of its volatility the foodstuff should not be subjected to an open-container cooking or drying step after the methylsulfonylmethane is admixed therewith. In the case of dry foodstuffs, the volatility of methylsulfonylmethane can, if desired, be counteracted by encapsulating or coating the individual particles of methylsulfonylmethane prior to its addition to the foodstuff with a continuous coating, e.g., a natural waxy or synthetic polymeric film, which is dissolvable or removable in the digestive system. Techniques for coating moisture-unstable products intended for ingestion, to protect them from the adverse effects of atmospheric moisture and/or oxygen, are well-known in the pharmaceutical arts and can be employed to inhibit the loss of the methylsulfonylmethane from the foodstuff prior to its ingestion by evaporation. Loss of the methylsulfonylmethane from wet processed foodstuff products can be reduced by conducting all heating steps and storing the processed foodstuff in a sealed container.

In addition to or alternative to being administered in admixture with one or more of the foodstuffs ingested by the animal, as described more fully elsewhere herein, methylsulfonylmethane can also be incorporated into the diet of humans and lower animals by ingesting the crystalline methylsulfonylmethane or a solution, e.g. aqueous, thereof separately from other foodstuffs, preferably, in unit dosage form, e.g., as a tablet, capsule, dragee or pill, as such or in admixture with the usual pharmaceutically acceptable excipients, diluents, tableting aids, etc., with tablets and capsules being preferred, especially those containing from 100 mg to 500 mg methylsulfonylmethane each.

Although human beings are the preferred recipients, other vertebrates, including mammals, e.g., domestic animals, such as horses, cows, sheep and pigs, pets, e.g., cats, dogs and fish, and wild animals kept in zoos, and fowls, e.g., chickens and other poultry, can be treated according to this invention. Both small children and adults, including geriatrics, gain a more beneficial balanced diet when methylsulfonylmethane levels match natural, unprocessed foods.

Although this invention is directed primarily to methylsulfonylmethane-containing foodstuff, methylsulfonylmethane is useful in other oral forms, e.g., mouth washes and toothpaste preparations, because of its chemical and light stability, low toxicity, good solvency, water solubility and dispersibility.

Methylsulfonylmethane, alone or in combination with an appropriate pharmaceutically active agent, has demonstrated usefulness when introduced into other body cavities, e.g., vaginally and rectally. Methylsulfonylmethane can be introduced into the lungs and bronchial tree as an aerosol of a solution thereof or as a sublimate produced by heating, which can be inhaled.

Since methylsulfonylmethane has an additive flavor or flavor enhancing property, e.g., for chocolate, soy sauce, salt, sweet vermouth and other alcoholic beverages, carbonated cola beverages, rye bread and other baked goods, it can be included in condiments and admixed or co-crystallized with NaCl or other particulate flavorings and condiments. Methylsulfonylmethane can also be safely administered by intravenous or parenteral injection. Additional benefits are seen when methylsulfonylmethane is provided in combination with the water-soluble vitamins.

Animal Feed

The animal feed aspect of this invention can be practiced in a number of ways. For example, the methylsulfonylmethane can be added to low moisture corn (approximately 14% moisture) at levels in the range of $15 \times 10^{-4}\%$ to 3.0%, usually 0.01% to 1.0%. Inasmuch as methylsulfonylmethane is a solid, the addition can be carried out in a batch feed mixer.

After the corn has been treated, it can be used as such as an animal feed or it can be stored and used at a later date or it can be mixed with other ingredients, e.g., alfalfa meal, soybean meal, minerals and vitamins. The resultant mixture can be used as such as an animal feed or it can be pelleted and the pellets employed as an animal feed.

One method of preparing pellets is to grind corn, alfalfa meal, soybean meal, minerals and vitamins, add steam to bring the moisture content up to 16% water and then allow the mixture to stand and cool so that the final moisture content is around 14%. Methylsulfonylmethane is added to this mixture, preferably before pelleting in proportions sufficient to give a mixed feed containing the desired concentration of methylsulfonylmethane. The corn admixed with the methylsulfonylmethane can be used as whole kernels or it can be cracked or ground and used as such or in mixed feeds. In case the product is to be used without lengthy storage, the methylsulfonylmethane content can be as low as $15 \times 10^{-4}\%$ to 3.0%. Because of the volatility of the methylsulfonylmethane, if the corn or feed is stored prior to use, the methylsulfonylmethane content is preferably about 0.01% to 5%.

The methylsulfonylmethane can also be administered to the animals in the form of a solution in their drinking water, e.g., 0.01% to 3%, preferably 0.1% to 2% by weight.

The methylsulfonylmethane can also be added to the animal feed immediately prior to feeding time, e.g., by spraying a solution thereof into the feed or stirring crystalline methylsulfonylmethane into the feed in amounts which will provide the desired ingested amount.

The animal feed aspect of this invention is particularly important where it is desired to improve the overall appearance of or maintain the health of herbivorous animals, especially beef cattle, dairy cattle, hogs, horses, sheep, goats and fowl. It is particularly useful in reducing the incidence of stress-related deaths, e.g., due to close confinement.

The methylsulfonylmethane is usually provided in the animal's normal feed rations, periodically throughout the day or on successive days, or both, e.g., for 2 to 21 days or even longer. The daily food ration appropriate for the animal being fed is supplemented with an amount of methylsulfonylmethane calculated to correspond to a predetermined amount per total body weight of the animals being fed. The exact amount of methylsulfonylmethane ingested each day is not always critical, particularly when methylsulfonylmethane administration is over an extended period of days, because the ingested methylsulfonylmethane accumulates in the body tissues and fluids, i.e., reaches an effective titer. Methylsulfonylmethane-supplemented rations providing levels of as low as 0.5–1 mg/kg animal body weight are sometimes effective and levels as high as 300 mg/kg body weight or more are well tolerated. The usual target level per individual animal is about 0.2–2.0 mg/kg body weight preferably 0.5–1.0 mg per kg body weight. Total daily supplements corresponding to up to about 1 gm/kg body weight or more, are preferably employed, depending on the degree of deficiency. Healthy animals often have methylsulfonylmethane blood levels of at least 1 ppm, and desirably, enough methylsulfonylmethane is provided to raise blood levels to above 1 ppm. The oral ingestion of amounts of methylsulfonylmethane in excess of that required to elevate blood levels is not harmful because of the extremely non-toxic nature of methylsulfonylmethane.

Because methylsulfonylmethane is naturally present in the body fluids and tissues of animals, its mode of action resembles that of a vitamin-like dietary supplement. Although methylsulfonylmethane has not yet been established to be a vitamin, at least a vitamin deficiency-type disease has not yet been proved to occur in animals with abnormally low methylsulfonylmethane blood levels, it does have a vitamin-like moderating or normalizing activity correlation between abnormal physiological symptoms and low methylsulfonylmethane blood levels. Whether this is due to the inability of such animals to adequately store methylsulfonylmethane from natural sources thereof, to inadequate amounts of methylsulfonylmethane in the diet of those animals or the depletion of the methylsulfonylmethane usually present in the body as a result of the abnormal condition, is not known. Whatever the reason, the oral ingestion of methylsulfonylmethane in sufficient amounts will ultimately bring methylsulfonylmethane levels to or above those usually present in healthy animals and will ameliorate a variety of symptoms associated with stress.

Like vitamin C, glucose and other substances normally present in animal diets, methylsulfonylmethane exhibits remarkably low acute and chronic toxicity in the hosts diet. Primates with high (greater than 1 gm/kg body wt.) methylsulfonylmethane blood levels for at least two years lack evidence of methylsulfonylmethane toxicity.

Although methylsulfonylmethane is found as a natural constituent of foodstuffs, like vitamin D, the principal supply in animals is believed to be synthesized by the body using dimethyl sulfide or one of its naturally occurring precursor salts as commonly found in meat, fish, vegetables and fruit. Too low a body concentration of methylsulfonylmethane results in adverse physical and psychological stress, tissue and organ malfunction, fatigue and increased susceptibility to diseases.

Based on the excretion rate from young compared with older animals, methylsulfonylmethane appears to be present in lowering concentrations with increasing age. Generally, with maturity, there is less than 0.5 ppm methylsulfonylmethane in the humoral fluid. This may explain why methylsulfonylmethane has proved generally more useful as a dietary supplement with mature animals, in whom naturally occurring levels of methylsulfonylmethane, generally are lower than optimum for providing optimum protection of the organism from stress challenge. A conventional diet does not supply the minimum requirement for optimum health. For example, unprocessed milk, one natural source of methylsulfonylmethane, contains only about 2–5 ppm depending on the source. To obtain and retain a minimum blood level of methylsulfonylmethane of about 1 ppm, animals would be required to ingest an impractically large amount of this or any other single unprocessed food product. According to this invention, the diet of a methylsulfonylmethane-deficient animal is supplemented with sufficient methylsulfonylmethane to provide blood levels of more than 1 ppm and, where health is threatened, a level of 10–20 ppm or higher.

Additional benefits are seen when methylsulfonylmethane is provided in combination with the water-soluble vitamins.

Conventional feedstuffs for meat producing animals comprise supplemented complete or basal animal feeds or, alternatively, premixes for preparing such feeds. The carrier or basal feed is usually hay or corn derived but may include dried fermentation residue, alfalfa, cotton-seed, barley meal, soybean meal, corn meal, rice hulls, molasses, mineral salts, vitamins, silages, beet pulp, citrus pulp, fish meal, oats, rice bran, milo, sesame meal, milk or other standard animal feed ingredients. In premix compositions the other ingredients are mixed in high concentration with a carrier ingredient which is usually desirable in the complete feed such as soybean meal, corn oil, ground corn, barley, mineral mixtures such as vermiculite or diatomaceous earth, corn gluten meal, corn distillers solubles or soyflour. As examples of the livestock feed normally ingested per meat producing animal per day are: sheep 3–4 lbs., feed lot steer 20–25 lbs., swine 1–8 lbs., poultry 0.03–1 lb. The methylsulfonylmethane contents of these animals feed is adjusted to provide the desired mg/kg body weight methylsulfonylmethane daily ingestion rate.

Dairy cattle typically are fed two different types of vegetable feed, the first roughage including hay and corn silage and the second, a supplemental ration usually containing ingredients of the type listed above. In the case of an average dairy cow, this supplemented ration might be within the range of 10 to 20 pounds per day.

Feed intended for chickens would not contain added roughage. The ratio of starch to protein would depend on whether the bird is being raised for meat or is a hen producing eggs.

Also well known and readily available commercially are pet foods for dogs, cats, hamsters, etc., and fish food, etc.

As previously stated, methylsulfonylmethane when included in animal feed rations is useful as a flavor enhancer, as a health maintainer and in preventing stress death in the animals.

Stress deaths are a well known phenomena for some species of animals, especially chickens, because of the crowded manner in which they are raised and transported and the generally rough treatment given to them in transferring them from one area to another; turkeys, because of their temperament; and fish, especially species of tropical fish which are normally sold for aquariums, because of their extreme sensitivity to changes in the composition of or temperature of their water. Methylsulfonylmethane is particularly useful in reducing the incidence of stress-related deaths when administered daily for from 7 to 90 days, preferably 14 to 28 days prior to the animals being exposed to the death-inducing stress, and during the period of such stress, e.g., at dosages from about 0.01 to 10 mg/kg, preferably from about 0.01 to 5 mg/kg body weight per day.

The following are pharmacological uses for methylsulfonylmethane in addition to its use in foodstuffs as described hereinabove:

1. Reducing the adverse response to inhalant allergens. This action may be due entirely or in part to a physical blocking action. Labeled 35-S dimethyl sulfone binds tightly to the surface of mucous membranes and by autoradiography, the membranes appears to be coated, as with a paint.
2. Controlling problems associated with gastric hyperacidity, e.g., relieving epigastric pain.
3. Providing relief from chronic constipation.
4. Reducing or eliminating hypersensitivity problems associated with oral medications, such as non-steroidal antiarthritic agents. This effect may be the result of the interaction of the methylsulfonylmethane with plasma prostaglandin F2.
5. Providing relief from the symptoms of lung dysfunction, e.g., by plasticizing effect on the membrane surface of the lung involved in gas exchange.
6. Controlling parasitic infections associated with the intestinal or urinogenital tract, e.g., those caused by giardia or trichomonads. Methylsulfonylmethane also has a beneficial effect in the treatment of disease conditions caused by a spectrum of other micro-organisms.
7. Mood elevators, e.g., for the terminally ill.
8. Improving the chemical profile of arthritic patients, e.g., providing relief from pain and stiffness, reduced swelling and inflammation, coupled with a return of blood chemistry towards normalcy, for example, a RH titer drop from 600+ to 300 or lower.
9. Relieving leg and back cramps, muscle spasms and general soreness, particularly in the geriatric patient, and in the premier athlete after competition stress.
10. Reduction in hypertension.
11. Promoting remission in myositis ossificous generalis (a rare, genetic/autoimmune dysfunction).
12. Improving the overall health of domestic and farm animals, e.g., dairy and beef cattle, horses, pigs, sheep, goats, chickens and turkeys whose caloric intake is predominantly or exclusively processed food rather than growing grasses and plants.
13. Reducing the incidence of stress deaths in animals raised and/or shipped in crowded or otherwise stressful conditions.

Leg Cramps

Methylsulfonylmethane has the surprising ability to reduce the incidence of or eliminate entirely muscle cramps, leg and back cramps, particularly in geriatric patients who experience such cramps at night and after long periods of inactivity, e.g., while sitting, and leg cramps in athletes, e.g., runners, football, basketball and soccer players, who experience severe leg cramps during participation in their sport. Ingesting methylsulfonylmethane, either in pharmaceutical composition form or in admixture with one or more foodstuffs for from 1 to 90 days will reduce the incidence of such cramps or eliminate them entirely.

Parasitic Infections

Methylsulfonylmethane has an ameliorating or curing effect on a variety of parasitic systemic microbial infections. Efficacy can be determined by in vitro testing to determine growth inhibition or killing of the specific organism by exposure to methylsulfonylmethane at various concentrations in an otherwise acceptable growth-maintaining in vitro media for the organism. If inhibition or death of the organism occurs when exposed to methylsulfonylmethane at concentrations below about 100 ppm, the methylsulfonylmethane will exhibit in vivo activity against that organism. Examples of parasitic infections susceptible to treatment with methylsulfonylmethane are those commonly associated with infection of the intestinal or urinogenital tract, e.g., Nematodes, Trichomonas vaginalis, Giardia, Enterobius and other intestinal worms, systemic infections by Histoplasma capsulation, Cocoidioides, Toxoplasm and other in vitro susceptible organisms.

Intravenous Administration

In U.S. Pat. No. 4,296,130, I teach that methylsulfonylmethane is so inert and non-toxic that aqueous solutions thereof can be used as a blood diluent. In healthy humans or other animals having adequately high methylsulfonylmethane blood levels, methylsulfonylmethane is in fact "inert" in the sense the term is used in that patent. However, in acutely ill patients, dramatic beneficial benefits are often obtained by the intravenous administration of large doses of methylsulfonylmethane. For example, rheumatoid arthritic patients suffering from a flair-up of the disease which produces intense pain or crippling swelling of the joints or both achieve prompt relief, even those patients who obtain only minimal or delayed benefits from oral ingestion of methylsulfonylmethane.

Apparently, when a patient is in an acute stage of intense pain-producing disease, such as rheumatoid arthritis, osteoporosis, degenerative disc syndrome, an autoimmune disease or metathesized carcinoma, which produces intense pain, the relief from pain from oral ingestion of methylsulfonylmethane is sometimes too subtle or takes too long for the patient to obtain reasonably prompt subjective benefits therefrom. In contradistinction, intravenous administration of methylsulfonylmethane gives prompt, i.e., within hours and often within minutes, relief from pain and often dramatic benefits, e.g., a significant reduction in the crippling effects of rheumatoid arthritis.

Therefore, in one aspect this invention relates to a method for rapidly ameliorating at least the pain associated with an intense pain-producing disease by the intravenous administration of methylsulfonylmethane in an amount effective to ameliorate the pain.

The amount of methylsulfonylmethane intravenously administered can vary substantially because of its lack of toxicity and adverse side effects. Individual doses can vary from about 0.01 to 2 gm/kg, preferably from about 0.1 to 1 gm/kg, on a body weight basis, the usual dosage range is about 0.25 to 0.75 gm/kg, preferably about 0.5 gm/kg.

When large amounts are administered, e.g., in the order of 1 g/kg of body weight or more, i.e., infusion of 5% to 10% solution of methylsulfonylmethane in water, physiological saline or 5% dextrose is preferred. The rate of administration is preferably no greater than about 1 gm/kg/hr, although infusion rates as high as 2 gm/kg/hr are tolerated by patients, except for lightheadedness of the type experienced by some blood donors is experienced by some patients at this rate.

Because methylsulfonylmethane is very rapidly excreted, the intravenous administration can be repeated frequently, e.g., every 12-24 hours. However, one i.v. administration often suffices to achieve amelioration of pain and other symptoms, which remission can be maintained for weeks or months with orally ingested methylsulfonylmethane.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Example 1 - Human Food

During the cooling step of a conventional continuous milk pasteurization process, inject a sterile 25% aqueous solution of methylsulfonylmethane into the pasteurized milk at a rate which imparts a final concentration thereof in the milk of about 15 ppm.

Example 2 - Human Food

Incorporate prior to cooking, along with the NaCl, sugar or any condiment which is added to a vegetable or fruit cooked under pressure in a sealed can, e.g., corn, peas, tomatoes, green beans, peaches, pears, pineapples, apple sauce, etc., an amount of methylsulfonylmethane which provides a concentration thereof in the cooked product of about 5 ppm.

Example 3 - Equine Feed

Calcium/phosphorous balance is critical in the horse, where these elements comprise roughly 70% of the mineral content of the horse's body. Calcium deficiency, or the reverse, viz., phosphorous excess, is undesirable. Phosphorous excess in feed will decrease intestinal absorption, resulting in lowered blood plasma calcium. One result is a stimulation in the dietary deficiency condition called nutritional secondary hyperparathyroidism. Calcium denied for bone development results in an enlargement of structurally defective fibrous tissue. In horse leg bones, it is called epiphysitis when stress inflammation is presented.

Two colts and four fillies were studied, all diagnosed as having nutritional secondary hyperparathyroidism with obvious epiphysitis. Each was provided with 12 grams of methylsulfonylmethane twice daily in a bran/molasses blend intermixed with their standard dry feed prior to feeding. The supplemented feed was well accepted. All signs and symptoms of this nutritional deficiency disease was corrected in from seven to ten days. Conventional treatment for correcting dietary calcium deficiency requires a minimum of 60-90 days before relief from inflammation is obtained. Except for the added methylsulfonylmethane, there was no change in the diet of these seven horses. The added dietary factor corrected this easily recognizable dietary deficiency in all of the horses.

Example 4 - Equine Feed

A valuable breeding mare, treated for a respiratory infection developed bilateral fibrinous pleuritis, easily heard with auscultation of the chest. After six weeks therapy with a combination of conventional antibiotics and anti-inflammatory drugs, there was little if any improvement. Conventional therapy was terminated. Methylsulfonylmethane was added to the diet of this refractory case (24 g, twice daily, over a period of 5 days). This was the only special treatment given. By the fifth day the animal no longer demonstrated pain and the shallow, rapid breathing returned to normal. Auscultation of the chest was negative. This horse was followed over the next two years and was judged normal and healthy.

Example 5 - Methylsulfonylmethane in Tobacco

Distribute methylsulfonylmethane in the tobacco used to provide cigarettes at the rate of 100 ppm by weight by spraying the tobacco just prior to being formed into cigarettes with a 10 % ethanolic solution of methylsulfonylmethane at the rate of one ml/kg.

The inhaled smoke from such cigarettes includes sublimed methylsulfonylmethane, which counteracts the adverse effect of the smoke on the lung mucosa. Also, a significant number of smokers find the flavor and taste of the cigarette more desirable than otherwise identical cigarettes lacking the methylsulfonylmethane.

Example 6 - Nail Growth In Animals

Rate of nail growth is an indication of the overall health of an animal. To determine the effect of methylsulfonylmethane on nail growth, two litter mate female labradors, age 8.5 months, were maintained in side by side straw bedded cages. Before any testing, the front paws of each dog were embedded in partially set plaster of paris, allowing the animals to exert full body weight, thereby obtaining good clear impressions of paw pads and nail length.

Each dog was fed Purina dog chow and water ad lib for 45 days. One of the dogs, (Animal A) had no ration change and the other (Animal B) was supplied only with water containing 5% of methylsulfonylmethane dissolved therein. After 45 days, plaster impressions of the front paws of each dog were again taken. Once the plaster had fully hardened the pre- and post-testing castings of each animal were compared. The straw bedding protected both animals from normal nail wear. On visual examination, the nails of Animal B, the animal receiving methylsulfonylmethane in its water, were obviously longer. Upon comparing the castings it was seen that Animal B had nails that averaged about 1/8th inch greater length than those of Animal A.

The hair, horn, and nails of animals can contain 5% or more sulfur based on elemental analysis. This test indicates that the sulfur of methylsulfonylmethane, roughly ⅓ the molecule's weight, is utilized beneficially in stimulating at least nail growth.

Example 7 - Animal Coats

The coats of animals A and B of Example 6 were examined by three individuals. Each judged the coat of Animal B to be superior, based on thickness and the shiny appearance generally associated with good health.

Example 8 - Animal Coats

Ten 4-week old guinea pigs were housed in individual metal cages in a standard temperature room with a 12-hour light/dark cycle and acclimated over a 5-day period of feeding Purina guinea pig chow with water ad lib.

On day six, five animals were marked on the belly with red and the other five with blue water-insoluble ink. The marks were not visible when the animals were observed from above. Each animal after marking was returned to its cage and a corresponding red or blue tape affixed to the animal's watering bottle. The red marked bottles were maintained with tap water and the blue marked bottles were filled with tap water containing 2 wt.% methylsulfonylmethane. During a 28 day period, the animals were fed and allowed access to their water or water +2% methylsulfonylmethane, respectively, ad lib. On day 28, the animals were placed in common confinement on a well lighted table. Four individuals, totally unfamiliar with the test and its purpose were asked to evaluate the coat of each animal. Animals at each evaluation were removed by the evaluator and placed into one of two groups based on better or poorer quality of the animal's coat without seeing the color on the animal's belly. Three of the four evaluators quickly selected five animals with superior coats, all of which were later determined to bear a blue belly mark, i.e., the methylsulfonylmethane treated group. The fourth evaluator selected three animals with a blue belly mark as having superior coats but concluded he could not distinguish better from the poorer with the remaining seven animals. Despite the failure of one evaluator to clearly distinguish all animals given methylsulfonylmethane from the controls, the testing demonstrated that a generally visible improvement is seen in the coat of a guinea pig having methylsulfonylmethane as an added food in its ration.

Example 9 - Stress Death in Chickens

Feed broiler chickens, no more than a few days old, were fed one of two diets, viz., standard feed or standard feed plus 0.2wt.% methylsulfonylmethane for a period of 30 days. There will be a significant difference between the stress death rates in the two lots during that period. With those fed unmodified feed, the death rate will be normal, viz., about 10%, whereas with methylsulfonylmethane modified feed the death rate will be less than 1%.

Example 10 - Stress Death in Fish

Fish of any species demonstrate stress death in crowded conditions. Commercially valuable species, such as salmonids, are very prone to stress-death during confinement in hatcheries or aquaculture farms.

62 Goldfish, about 2 inches long, were divided into two 31 population lots and placed in acclimated aquariums (2) maintained at 50° F. On receipt of the fish, two small one gallon aquariums were filled with tap water and stablized for 5 days by aeration with an aerator/filter combination connected to a common aquarium air pump. Air delivery during the test period was standardized at 100 ml of air per minute. From a 1 oz. package of "Wardleys" goldfish food two 10 gram samples were removed. One sample was untreated and the other was moistened with about one ml of pure ethanol containing 0.2 gram methylsulfonylmethane in solution. The feed absorbed all the methylsulfonylmethane (the lot after air drying for 48 hours weighed 10.2 grams). Both feeds were pulverized to a coarse powder suitable for feeding small fish.

The 31 fish in each of the two holding aquariums were identified as batch A and batch B. During the acclimatization and test periods the batch A fish were fed 0.5 gram of untreated "Wardleys" food once daily. Batch B fish were fed 0.5 gram of the feed containing the methylsulfonylmethane during the acclimatization and test periods. Neither batch A nor B consumed all of the feed as some eventually collected in the fiberglass filter. However, most of each feeding was consumed in the first 5-10 minutes after delivery. During the 5th day, 25 fish of batch A were transferred to one small aquarium (designated A) and 25 fish of batch B were moved to the other small aquarium (designated B). Before transfer, each aquarium was temperature adjusted with ice to 41° F. The water was allowed to return to ambient, e.g., to 50° F., after the fish were added to the tank. The fish of both batches were thus subject to a total of 9° F. temperature change, which stressed the fish. Feeding was resumed after starving them for one day in the small tanks. By day ten, (five of them in the small aquariums), there had been a total of 11 deaths in aquarium A (control) and one death in aquarium B.

The combination of impressed negative temperature, tank transfers, marginal oxygenation of the tanks, and confinement of a beginning population of 25 fish/gallon aquarium imposed sufficient stress to kill nearly ½ the control fish. The addition of only 2% by weight of methylsulfonylmethane to the feed reduced stress significantly.

Example 11 - Oral Hygiene

Subjects not having professional dental cleaning for at least four-six months and demonstrating minor yet discernable gum inflammation, probably due to plaque irritation, were given either a paste (Colgate tooth paste) prepared by combining a commercial dental product with methylsulfonylmethane on a 50/50 w/w basis. Subjects cleansed their teeth on a twice daily regimen. Following one week use, the oral mucosa of all subjects was free of signs of inflammation. One subject (T.K., M 22) troubled with recurring canker sores reported freedom from this problem during and after the one month testing was terminated. Methylsulfonylmethane, a solvent and dispersant in aqueous media, was shown to be an excellent agent alone for cleansing of teeth and the buccal cavity.

Subjects of this test with a viscid mucoid nasopharyngeal discharge experience a reduction in the viscosity of the mucous and generally a productive cough. Interestingly, two subjects with a restricted sense of smell found a sharpening of this sense while methylsulfonylmethane was being evaluated by them in a gargle. Critical observers noted their sense of taste was improved.

Bad breath associated with smoking or food, such as onion and garlic, is reduced or eliminated by cleansing the teeth and mouth with methylsulfonylmethane in water, saline solution or a conventional oral hygiene product.

Example 12 - Maintenance of Good Health 14 subjects of both sexes, all in apparent good health, ages 33×59, were given oral methylsulfonylmethane in amounts ranging from 250 to 500 mg daily which maintained their blood levels above 1 ppm. These individuals were continued on methylsulfonylmethane, taken as a solution in orange juice for periods of from about seven months to over one year. None of the 14 became ill during this testing and each reported feeling better and stronger with increased endurance while methylsulfonylmethane was a part of their diet.

Example 13 - Connective Tissue and Dermatological Disorders

Primary and secondary pruritis, acne (including Grade 4), acne rosacea and diverse other dermatological problems which are often allergy related respond favorably to a diet supplemented with methylsulfonylmethane. Pruritis due to various causes and acne respond promptly to diet supplemented levels of about 100-1000 mg per day. Teenagers found methylsulfonylmethane in cola drinks a particularly acceptable satisfactory combination when treating acne. With rosacea, visual improvement was much slower. In one subject (J.H., F 51) daily ingestion of 500 mg methylsulfonylmethane for at least several weeks was required before telangiectasis diminished.

Example 14 - Inflammation of the Eye

A 15% solution of methylsulfonylmethane in isotonic saline was a soothing treatment for the eye following accidental injury due to particulate matter in the eye as dust or pollen. A rabbit eye, irritated with aqueous sodium lauryl sulfate, quickly cleared when treated every hour with 10% aqueous solution of methylsulfonylmethane.

Example 15 - Pain Associated With Systemic Inflammatory Disorders

Individuals presenting signs and symptoms of pain and inflammation associated with various musculoskeletal system disorders reported substantial and long lasting relief while including from about 100 up to about 5,000 mg of methylsulfonylmethane per day in their daily diet. Most, trying methylsulfonylmethane first alone and then in combination with ascorbic acid, reported greater benefit with the combination. The combination of methylsulfonylmethane with ascorbic acid was seen to be particularly useful in correcting night leg cramps. Migrane sufferers have obtained substantial relief at oral dose levels of 50-500 mg per day.

One subject (M.P., F 81), presented chronic arthritis with painful involvement of the lower trunk. Over the years she had evaluated most new antiarthritic, analgesic drugs with disappointing results. She included methylsulfonylmethane ($\frac{1}{4}$ tsp. daily) in her diet and found almost total pain relief by the end of the second week. After ingesting methylsulfonylmethane daily at $\frac{1}{4}$-$\frac{1}{2}$ tsp. for about 16 months, the subject is enjoying a substantially pain-free life.

Example 16 - Mental Normalcy

In man, mental normalcy is demonstrated by alertness with inner calmness which is not subject to sharp swings in mood change. Individuals on methylsulfonylmethane generally reported increased alertness, a plateau of mood changes, and particularly very infrequent depression. A few subjects on medication intermittently for depression observed that methylsulfonylmethane relieved depression within hours rather than days, as had been their prior experience with antidepression medication. Students reported that while taking methylsulfonylmethane, their ability to concentrate is enhanced. Methylsulfonylmethane therefore is useful in conjunction with CNS therapeutants. The most useful application for methylsulfonylmethane seen to date in the field of mental normalizing is as an aid to the terminally ill, to relieve anxiety and depression.

To a chronically or terminally ill patient suffering from mental depression, administer 1000 mg/kg body weight of methylsulfonylmethane daily, in tablet or capsule form, dissolved in water or a cold beverage, or admixed in a cold food. Within 12.-hours to 2 days, a significant improvement in the mental attitude of the patient will be noted.

Example 17 - Wound Healing

Four sets of 5 hamsters were subject to scarification of the right cheek pouch, using standard methodology. One week prior to pouch injury, one set was started on a daily regimen of 0.1 gm/kg of methylsulfonylmethane in the diet of standard hamster feed, a second group was given 0.1 gm/kg of methylsulfonylmethane plus 100 mg of ascorbic acid in the same feed, a third group was given only 100 mg of ascorbic acid in the same feed, and the last group, fed only the feed, was held as control. Daily post-scarification examination was made to determine the rate of injury repair. After 36 hours, the animals receiving methylsulfonylmethane plus vitamin C orally had sharply reduced inflammation about the wounds and prominent healing granulation. This baseline result was matched by day three with both methylsulfonylmethane alone and vitamin C alone treated subjects. By day.4 and 5, controls (no medication) matched the healing status seen at 36 hours with those animals receiving the methylsulfonylmethane/ vitamin C combination.

Example 18 - Diet Supplement in Animals

Immature laboratory animals, including dogs, consistently gained weight at a greater rate over controls where methylsulfonylmethane was included in their water and/or food. This was observed at both low and high dosage levels, viz., about 60 and about 500 mg/day/kg body wt. A possible explanation for this is that any minor allergic response to the diet was neutralized by the methylsulfonylmethane. Additionally, the fur quality improved and somewhat faster nail growth was noted. Weight increases were not seen with adult animals during comparable feeding experiments.

Example 19 - Parasite Infection (Enterobius)

Laboratory mice determined by fecal cast examination to have pin worms were given commercial feed and drinking water, ad lib, both of which contained 2% by wt. methylsulfonylmethane. Examination 17 days after test initiation indicated the fecal cast were free of worms and eggs. The blood level of methylsulfonylmethane in one animal examined exceeded 30 ppm.

Methylsulfonylmethane's ability in returning parasite susceptible tissue to normalcy where host injury is minimal or nil, suggests that methylsulfonylmethane in the diet aids in overcoming varied microbial infections, by strengthening body resistance thereto rather than by direct attack on the organism.

Methylsulfonylmethane antagonizes anticholinesterases in vivo and possesses weak in vitro antibacterial action, for example, against Escherichia coli, Leuconostoc citrovorum, Salmonello typhimurium, Staphlococcus aureus and Streptococcus thermophilus. It is a potent antifungal agent, demonstrating good antiparasitic activity at 500 ppm against Aspergillus niger, Phytophthora cinnamomi and Sclerotium rolfsii. While not as potent or toxic to microbial populations as specific drug agents, by reason of its extremely low host systemic toxicity, methylsulfonylmethane contrasts sharply with present antiinfective therapeutants and methodology. It is doubtful if chemical resistance will develop with infective agents controlled by high, but safe, systemic levels of methylsulfonylmethane.

One can safely administer 1–2 grams/kg body wt. of methylsulfonylmethane on a daily basis (equal to 1000–2000 ppm w/w basis). One therefore builds a safely tolerated blood level of about 4000 ppm, which level is highly toxic to many infective organism yet is harmless to the host. Methylsulfonylmethane provides a unique new therapeutic approach, used alone or with concurrent, conventional therapy.

An evaluation of methylsulfonylmethane as concurrent therapy with conventional anti-malaria drugs is indicated. Around one million humans die annually from this parasitic infection. Testing to date indicates that methylsulfonylmethane is a useful adjunct with the therapeutic modalities used to combat adverse health problems by increasing a subject's baseline resistance to adversity and moderating untoward effects associated with drugs, vaccines and physical assaults against illnesses as by radiation or hyperthermia.

Example 20 - Vascular Complications Associated With Diabetes

A subject (F.B., M 58), diagnosed to have diabetes mellitus 22 years earlier was seen with a serious vascular complication. Arteriosclerosis has decreased the arterial blood supply to the lower limbs, resulting in chronically cold feet and intermittent claudication. In addition, the subject had suffered a bruise to the foot which was not healing. This subject received 500 mg of methylsulfonylmethane with 250 mg of ascorbic acid twice daily over a period of 21 days. The first observed improvement was the healing rate of the bruise. By the end of the third week, the cold foot problem was partially relieved and the subject was able to double his walking distance without undo tiring. Post treatment laboratory workup suggested a possibility that his insulin requirement could be reduced.

Example 21 - Acute Pain

Methylsulfonylmethane administered orally has proven useful in relieving acute pain in the mid-back region of an adult male caused by calculi obstructed ureter (single 1.5 gm dose dissolved in warm water) and pain spasms in the lower abdomen region of an adult female resulting from an accidental blow to the abdomen (two 1 gm doses in warm water at 4-hour intervals).

Example 22 - Low Platelet Count

Methylsulfonylmethane administered orally raised the platelet count of an adult female with lupus erythematosus from 84,000 (after prednisone therapy) to 200,000 over a 2-year period (1.5 gm/day in 3 doses).

Example 23 - Sun and Wind Burn

Persons ingesting from 0.5–2 gm/day of methylsulfonylmethane suffered only mildly from about 4 hours of exposure to summer sun and wind, whereas their companions who had not ingested methylsulfonylmethane were severely sun- and wind-burned.

Example 24 - Pleuritis

Bilateral fibrinous pleuritis developed in a breeding mare with a respiratory infection, which did not respond to six weeks of conventional antibiotic and antiinflammatory therapy, responded favorably (normal breathing, negative ausculation of the chest) after five days of methylsulfonylmethane ($2 \times 12$ gm/day in diet).

Example 25 - Post-Athletic Activity Fatigue

The physical fatigue syndrome following intense athletic activity in competitive sports which usually persists for 8–10 days in athletes was gone in 2–3 days in individuals who had ingested methylsulfonylmethane (from 1–2 gm/day in split dosages) for the preceding six months.

Example 26 - Leg Cramps

Administer methylsulfonylmethane to a geriatric patient (over 65 years) suffering from chronic night leg cramps at the rate of 10 mg/kg/day, either in tablet or capsule form, as described in parent application S.N. 418,110, S.N. 584,354 or S.N. 601,771, or in admixture with one or more foodstuffs ingested daily by the patient, e.g., milk, coffee, tea, cold desserts, etc. Within about 2 days, the leg cramps will diminish in frequency or disappear.

Example 27 - Leg Cramps

Before a marathon race, administer methylsulfonylmethane to the runner for at least 7 days at the rate of 15 mg/kg/day. The likelihood of the runner experiencing severe leg cramp during or after the race will be significantly reduced.

Example 28 - Parasite Infection Control

Methylsulfonylmethane has highly variable toxicities for various nematodes. Based on this discovery, tests were conducted on several parasites adverse to the health of vertebrates.

(a) Trichomonas vaginalis

Strain ATCC No. 30001 was cultured in vitro employing diamonds tym medium. Methylsulfonylmethane was added thereto at levels varying from 5.5 to 109.3 mg/ml. At concentrations of 5.5 to 10.9 mg/ml, the methylsulfonylmethane had no effect on this protozoan. However, at 21.9 mg/ml it was inhibitory and all higher concentrations were lethal to this parasite Based on this assay, methylsulfonylmethane is about half as active as metronidazole HCL.

Methylsulfonylmethane was evaluated in vivo in conjunction with metronidazole HCL, given to two female subjects at a treatment level of 250 mg, taken every eight hours for ten days. Both had prior courses of therapy for this disorder without adequate response. Methylsulfonylmethane was administered as 500 mg capsules with each Flagyl dose during the treatment period. During this course of treatment, neither patient experienced stomach upset and nausea, although this was a side effect experienced by one subject during the first course of metronidazole HCL treatment alone.

The concurrent treatment of methylsulfonylmethane and Flagyl was successful in both cases, as confirmed by wet film examination. One subject was later reinfected by her sexual partner but the reinfection was cleared employing a daily douch of 5% aqueous methylsulfonylmethane for one week. The subject's partner was successfully treated with 500 mg of methylsulfonylmethane given twice daily for two weeks.

(b) Giardia lamblia

This microorganism is associated with "travelers diarrhea", particularly where persistent and refractory to antimicrobial therapy. Like many intestinal parasites, there is variable resistance to the organism by man, perhaps associated with receptor site availability and hence an immunological problem.

With this parasite, in vitro concentrations of methylsulfonylmethane of 1 mg/ml and lower demonstrated no significant inhibition of Giardia. However, at 20 mg/ml concentration, it was strongly inhibitory and concentrations above 40 mg/ml promptly killed the organism.

One subject with confirmed Giardia, apparently contacted from contaminated water in a primitive area, was given 500 mg of methylsulfonylmethane orally three times/24 hours X 14 days. By the eighth day he was asymptomatic. Two stool specimens collected one week apart were free of the organism.

(c) Enterobius

Laboratory mice determined by fecal cast examination to have pin worms were given 2 % by wt. of methylsulfonylmethane in both their commercial feed and drinking water, ad lib. Fecal examination seventeen days after test initiation indicated the feces were free of worms and eggs.

Example 29 - Treatment of Lung Dysfunction

Seven human subjects with respiratory deficiency were given methylsulfonylmethane by the oral route in amounts ranging from 250–1,500 mg/day, in single or divided units. Five presented emphysema believed associated with cigarette smoking. Two presented tumor involvement of the lung with additional function impairment due to pleural fluid accumulation.

Two of five subjects with emphysema had prior cardiorespiratory function tests and follow-up evaluations at six and eight weeks after starting a course of 500 mg/day orally of methylsulfonylmethane. Though both demonstrated several abnormal values prior to the test period, in particular lowered arterial oxygen tension, both had values in the normal range while ingesting methylsulfonylmethane.

A more striking improvement was seen in physical achievement values determined with all subjects. Prior to and during the test period, at approximately two-week intervals, all presenting emphysema were required to walk a measured distance compatible with their physical resources. Within 2–4 weeks of beginning the ingestion of methylsulfonylmethane, alone or with 1000 mg of ascorbic acid/day, all emphysema sufferers had at least doubled their "comfortable" walking distance. Both subjects seen with lung tumors were evaluated by attending physicians and nurses as well as family as being more alert, comfortable, and with a better outlook and attitude than before the test period. The lung cavity fluid problem of each subject disappeared during the first months of the test period. Both were on radiation/chemotherapy prior to including methylsulfonylmethane in their diet, but without apparent benefit.

Example 30 - Canine Arthritis and Other Sources of Pain

Methylsulfonylmethane was evaluated as an additive to the diet of older dogs of various breeds, all suffering from some form of arthritis and in some cases demonstrating other disorders. In each case the methylsulfonylmethane was admixed with the animal's food just prior to feeding.

(a) Dog A, a spayed, 15-year old German Shepherd, weighing 36 kg, demonstrated ataxia, virtual immobility with pain and joint stiffness. The animal was not responsive to cortisone or phenylbutazone. It was given 0.5 g/day of methylsulfonylmethane b.i.d. for 7 days without apparent benefit. Dosage was raised to 1.5 g/day b.i.d. and within 10 days the dog became freely mobile without evident discomfort nor demonstrated ataxia.

(b) Dog B, a male, black Labrador, weighing 27 kg, demonstrated severe musculoskeletal comprise of the hind quarters with urinary incontinence. This animal, although owned by a veterinarian, had not responded to a variety of therapeutic regimens over the previous 12 months. Methylsulfonylmethane was given to this dog in it's food at a level of 1.5 grams b.i.d. X 1 month. This dog derived no apparent benefit from methylsulfonylmethane, apparently due to the terminal nature of its illness.

(c) Dog C, a spayed, 14-year old German Shepherd, demonstrated severe arthritis of the back and legs. It was mobile but walked with obvious difficulty and discomfort. The animals was refractory to both cortisone and phenylbutazone. Methylsulfonylmethane was provided in the diet at a level of 0.5 grams b.i.d. There was gradual improvement in mobility over the first month. During the third month following methylsulfonylmethane supplementation of the diet, the dog demonstrated neither musculoskelatal restriction nor discomfort.

(d) Dog D, a female, mixed-breed Terrier, weighing 20 kg, demonstrated severe restriction in mobility and obvious discomfort with movement. The animal had not responded to either cortisone nor phenylbutazone and it's condition was deteriorating rapidly. Methysulfonylmethane was included in its diet at 1 gm/day b.i.d. After one week, the dog appeared to be pain-free. This dog has received methylsulfonylmethane in its diet for over six months and remains apparently healthy and frisky, requiring no medication.

Example 31 - Pain in Humans

The following patients suffering from intractible pain were given methylsulfonylmethane orally in the amounts and for the period of time set forth in the table below:

| Patient | Age | Sex | Diagnosis | Methylsulfonyl-methane Administration | Results |
|---|---|---|---|---|---|
| P.A. | 61 | F | Deg. Arth. | 1 g 4×/day × 19 months | pain relief |
| B.A. | 63 | F | Deg. Arth. | 0.25 g qid | pain relief |
| C.A. | 62 | M | Bursitis Chronic | 0.25 g bid × 3 months | 50% pain relief |
| M.A. | 55 | F | Rh. Arth. | 0.25 g bid × 9 months | pain relief |
| A.B. | 69 | F | Deg. Arth. | 0.5 bid × 18 months | pain relief |
| N.B. | 62 | M | Tendonitis | 0.25 g qid | reduced pain |
| D.B. | 35 | M | Low back pain | 0.5 g qid × 9 months | pain relief |
| I.B. | 62 | F | Multiple Sclerosis | 0.5 bid × 18 months | muscle pain reduction |

Deg. = Degenerative
Rh. = Rheumatoid
Arth. = Arthritis

Example 32 - Acute Pain in Humans

Methylsulfonylmethane was compared with codeine for the control of pain in subject J.H., a male, age 47, who awakened in the early morning with excruciating pain in the mid-back region, so intense it was difficult to pin-point a specific region. Subject had a past history of urinary calculi. Aspirin was ineffective but codeine provided acceptable relief during and after X-ray. Analgesic requirements were ½ grain codeine with aspirin every two hours. During day two, subject complained of mental confusion and codeine was withdrawn. The intense pain returned. The subject was given 1.5 g of methylsulfonylmethane dissolved in ½ glass of warm water. At 0.5 hours after taking the methylsulfonylmethane, the pain had essentially disappeared. Methylsulfonylmethane (1.5 g/day) was continued until the afternoon of the third day, when X-ray confirmed that the calculi yet obstructed the ureter. Subject was switched again to codeine with aspirin (½ grain X 2 hours). He reported less pain relief than was provided by methylsulfonylmethane. Methylsulfonylmethane was again administered (1.5 g×4 hours). On day 5 the calculi passed. Recovery was uneventful, requiring neither codeine, methylsulfonylmethane, nor a urinary tract antimicrobial.

Example 33 - Acute Pain in Humans

Codeine and methylsulfonylmethane were compared for the relief of pain in subject M.R., a female, age 26, who had sharp pain spasms in the lower abdominal region. Subject's appendix had been removed. Pain began after suffering an accidental traumatic blow to the abdomen during a volley ball game. Pyelogram examination indicated no obstruction. The pain pattern suggested ureter spasm. Codeine (2) plus ¼ grain with aspirin every 4 hours, provided some relief. The codeine/aspirin was discontinued and 1 g methylsulfonylmethane in warm water was given. A half-hour later all discomfort ceased. A second gram of methylsulfonylmethane in water was given 4 hours later, after which the subject continued pain free.

Example 34 - Intravenous Administration

For patients suffering from a serious chronic disease, e.g., an acute stage of rheumatoid arthritis or other acute inflammatory conditions or a patient in extreme pain, administer 1 gm/kg of methylsulfonylmethane i.v. as a 14% by wt. solution in sterile 5% dextrose solution, at the rate of 1 gm/kg/hr. Within 2-4 hours, significant subjective relief from the symptoms of the disease or condition is experienced by the patient, with the relief lasting for from 7 to 21 days.

Such massive i.v. administrations can be repeated as frequently as every 24 hours. Rates of dimethylsulfone administration as high as 2 gm/kg/hr are possible but may produce transient light-headedness in the patient.

Example 35 - Myositis Ossificans Generalis

An eight year old girl, A.Z., has demonstrated serious, irreversible myositis ossificans generalis. Her family belongs to a group of families each with a family member suffering from the disease. She has been on one teaspoon of methylsulfonylmethane orally, in split daily doses for nearly two years. The disease process has stopped, she is out of her wheelchair and is improving. No other child in the group is on methylsulfonylmethane and all are deteriorating physically. The disease cause is unknown but probably is a genetic/autoimmune type of disorder.

Example 36 - Resistance to DMBA-Induced Mammary Carcinoma

Forty-five female rats were stabilized to the laboratory and then divided into 3 groups of 15 each. Group 1 was designated control, Groups 2 and 3 were treated by topical application to the hair-free abdomen with a solution of the carcinogen dimethyl-benzanthracene (DMBA). All three groups were each fed a standard laboratory diet with water, ad lib. .Group 3 received in their standard diet 2% by wt. of methylsulfonylmethane. At 5 months post treatment with DMBA, both the control normal and Group 3 animals were free of mammary carcinoma. The Group 2 animals demonstrated chemically induced mammary cancers and were sacrificed.

Example 37 - Arresting the Development of Spontaneous Mouse Lymphomas

Laboratory mice genetically predisposed to lymphoma development were selected for this test. Humoral immunity participation was measured as was the effect of methylsulfonylmethane on an animal's life span. One set of 12 mice were maintained as controls. The treated (T) group received identical treatment except for their water given ad lib, which contained 3% by wt. of methylsulfonylmethane in solution.

By month 4 of this test, all controls were dead, due to lymphoma development. No T group mice had died by month 5. These normal balb/c strain mice of group T were tested for t-lymphocyte dependent (t-d) and t-lymphocyte independent (t-i) immune responses. Mice given methylsulfonylmethane demonstrated significantly enhancement of primary IgM and secondary IgG responses to sheep erythrocytes (SRBC), with significant suppression of the tnp-ficoll response. Based on these preliminary results, at high enough daily rates of ingestion, methylsulfonylmethane stimulates humoral immunity thereby providing protection to otherwise lethal spontaneous mouse lymphomas.

It can be seen from the foregoing and from the disclosure of S.N. 584,354 dealing with the ameliorating of the symptoms of stress and of allergies, which disclosure is incorporated herein by reference, that methylsulfonylmethane is useful in maintaining or improving the health of a variety of animals in a variety of ways.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for inhibiting nocturnal and arthritic activity-induced muscle cramps in a person having a propensity for such muscle cramps, which comprises orally ingesting an amount of methylsulfonylmethane effective to inhibit the muscle cramps.

2. A method according to claim 1, wherein the person is a geriatric experiencing reoccurring nocturnal muscle cramps.

3. A method according to claim 1, wherein at least about 10 mg of methylsulfonylmethane is ingested daily for a succession of days.

4. A method according to claim 3 of ameliorating the pain and discomfort associated with arthritis in an animal which comprises administering to an animal manifesting overt symptoms of the disease an amount of methylsulfonylmethane effective to ameliorate the pain.

5. A method according to claim 4, wherein the animal is a human being.

6. A method according to claim 5, wherein the arthritis is rheumatoid arthritis.

7. A method according to claim 6, wherein the methylsulfonylmethane is administered orally on successive days.

8. A method according to claim 4, wherein the animal is a domestic or farm animal.

9. A method according to claim 8, wherein the methylsulfonylmethane is admixed with the animal's feed.

10. A method according to claim 3 of alleviating intractible pain, which comprises administering intravenously to a patient suffering from a disease producing such pain an amount of methylsulfonylmethane effective to alleviate the pain.

11. A method according to claim 10, wherein the methylsulfonylmethane is administered as an aqueous solution over a period of at least ½ hour.

12. A method according to claim 10, wherein at least about 1 mg/kg of body weight of the methylsulfonylmethane is administered.

13. A method according to claim 10, wherein the disease is rheumatoid arthritis.

14. A method of ameliorating the pain and discomfort associated with arthritis, or with nocturnal or arthritic activity-induced muscle cramps, with gastric hyperactivity or with intractable pain, which comprises administering to the animal or individual suffering from such pain an amount of methylsulfonylmethane effective to ameliorate the pain.

* * * * *